United States Patent [19] [11] 4,267,116
Masi et al. [45] May 12, 1981

[54] NOVEL DAUNOMYCIN DERIVATIVES, THEIR AGLYCONES AND THE USE THEREOF

[75] Inventors: Paolo Masi; Antonino Suarato; Luigi Bernardi, all of Milan; Federico Arcamone, Nerviano, all of Italy

[73] Assignee: Farmitalia Carlo Erba S.p.A., Milan, Italy

[21] Appl. No.: 38,689

[22] Filed: May 14, 1979

Related U.S. Application Data

[62] Division of Ser. No. 901,358, May 1, 1978, Pat. No. 4,191,755.

[30] Foreign Application Priority Data

May 5, 1977 [GB] United Kingdom ............ 18775/77

[51] Int. Cl.³ .............................................. C07C 50/16
[52] U.S. Cl. ...................................... 260/376; 260/365
[58] Field of Search ........................ 260/365, 376, 592

[56] References Cited

U.S. PATENT DOCUMENTS

| | | | |
|---|---|---|---|
| 3,201,424 | 8/1965 | McCormick et al. ............... | 260/365 |
| 3,665,018 | 5/1972 | Jolles ..................................... | 260/365 |
| 3,686,163 | 8/1972 | Arcamone et al. .................. | 260/365 |
| 3,963,760 | 6/1976 | Bernardi et al. ..................... | 260/365 |
| 4,077,988 | 3/1978 | Arcamone et al. .................. | 260/376 |
| 4,191,756 | 3/1980 | Masi et al. ............................ | 424/180 |

*Primary Examiner*—Winston A. Douglas
*Assistant Examiner*—Raymond K. Covington
*Attorney, Agent, or Firm*—Hubbell, Cohen, Stiefel & Gross

[57] ABSTRACT

Daunomycin derivatives of the formula:

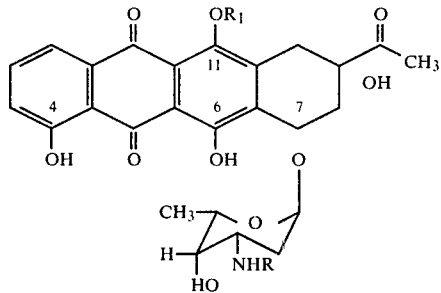

wherein $R_1$ is a lower alkyl having from 1 to 4 carbon atoms and R is hydrogen or a trifluoroacetyl group are useful in treating certain mammalian tumors.

4 Claims, No Drawings

NOVEL DAUNOMYCIN DERIVATIVES, THEIR AGLYCONES AND THE USE THEREOF

The invention described herein was made in the course of work under a grant from the United States Department of Health, Education and Welfare.

This is a division, of application Ser. No. 901,358, filed May 1, 1978, now U.S. Pat. No. 4,191,755.

BACKGROUND OF THE INVENTION

The invention relates to antitumor compounds which are anthracyclines, and in particular, to a new class of daunomycin derivatives and the aglycones thereof. The invention also relates to the use of these new compounds in treating mammalian tumors. Also within the scope of the invention are certain novel intermediates used in the preparation of the compounds of the invention.

SUMMARY OF THE INVENTION

The invention provides, in one aspect thereof, a new class of daunomycin derivatives of the formula I:

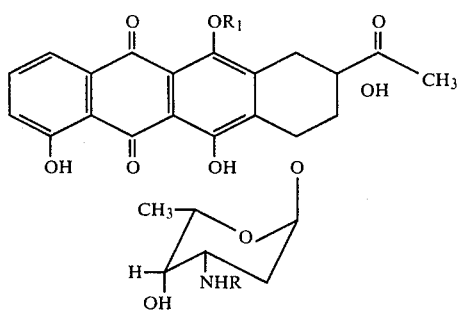

wherein $R_1$ is a lower alkyl having from 1 to 4 carbon atoms and R is hydrogen or a tirfluoroacetyl group.

These compounds are prepared from the respective aglycones of the formula II (which are derivatives of daunomycinone) by condensation with an N,O protected daunosamine derivative. The aglycones of the formula II:

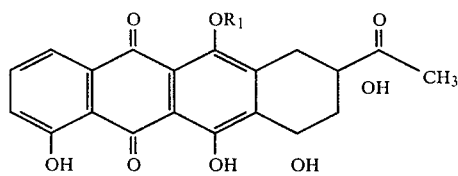

wherein $R_1$ is as defined above, are another aspect of the present invention.

The aglycones of the formula Ii are in turn prepared according to the following reaction sequence starting from intermediate V. The preparation of intermediate V from daunomycinone is described in co-pending application Ser. No. 901,359, filed May 1, 1978 and now Pat. No. 4,191,756, i.e., the U.S. counterpart of British application No. 18777/77.

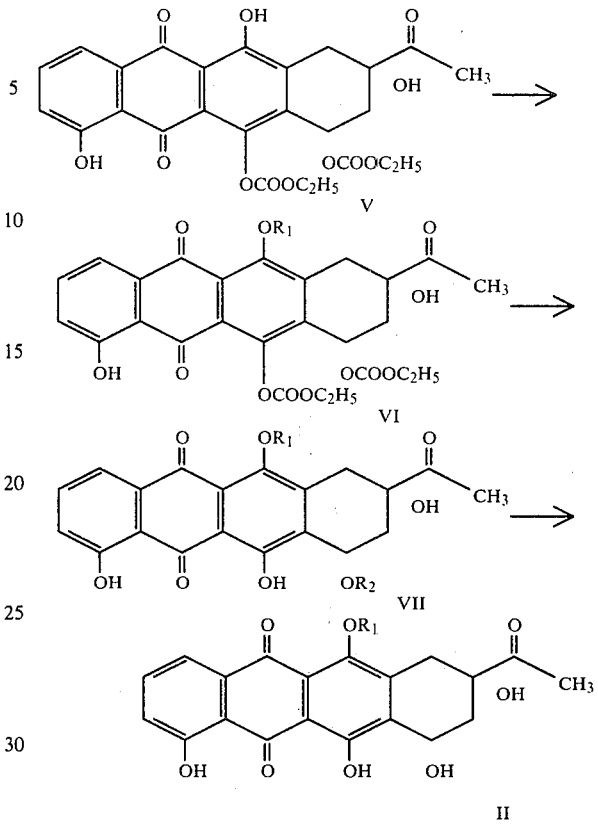

wherein $R_1$ is as defined above and $R_2$ is as defined hereinafter.

We have now surprisingly found that, under carefully controlled conditions, compound V can react in a highly regiospecific manner with a halide of the general formula $R_1$-Y, where $R_1$ is as defined above and Y is Cl, Br or I, to afford the monoether-derivative VI. Such selectivity was completely unexpected, since a much higher reactivity of the C-11-OH with respect to the C-4-OH is unpredictable a priori. The reaction is carried out in a solvent such as dichloromethane, chloroform, and the like in the presence of one equivalent of a base such as silver oxide and the like and a slight excess of the halide. Compound VI, on treatment with a dilute alkaline hydroxide or with an activated basic resin such as AG1—X2 and the like, gives rise to the bis-phenolic derivative VII, wherein $R_2$ is hydrogen when the reaction is carried out in an aqueous medium and preferably, is an alkyl group, when an alcohol, such as methanol, is used as the solvent. In the latter case, compound VII is hydrolyzed by mild exposure to aqueous trifluoroacetic acid to yield the new aglycones II together with small amounts of the 7-epimers thereof, which, in turn, can be transformed into aglycone Ii, having the 7-α-OH, following the equilibration procedure described in J. Am. Chem. Soc. 98, 1967 (1976). The biologically active glycosides of formula I are prepared by condensing an aglycone of the formula II (according to the procedure for the synthesis of glycoside linkages described in Belgian Pat. No. 842,930, owned by the unrecorded assignee hereof with a protected 1-halo-sugar in a suitable organic solvent such as dichloromethane or chloroform, in the presence of a soluble silver salt as a catalyst. In the present case, the aglycone II is condensed with 1-chloro-N,O-bis-trifluoroacetyldaunosamine, to form the N,O protected glycoside VIII:

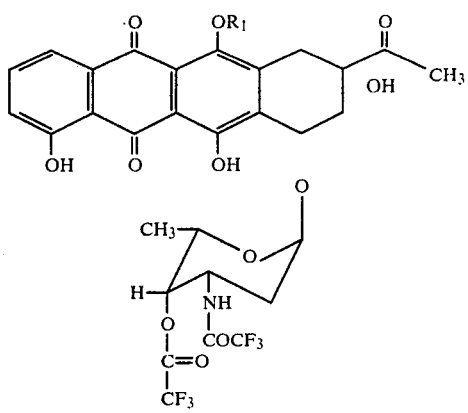

which, on treatment with methanol and a catalytic amount of triethylamine, is converted into the N-trifluoroacetyl protected glycoside which can be successively hydrolyzed, by mild exposure to a dilute alkaline base, to form the free glycosidic base which is finally isolated as the hydrochloride. The new compounds of the formula I, display antimitotic activity and are useful therapeutic agents for the treatment of certain mammalian tumors.

DESCRIPTION OF THE PREFERRED EMBODIMENTS

The following examples are given to illustrate the invention without, however, being a limitation thereof.

EXAMPLE 1

4-Demethoxy-4-hydroxy-11-deoxy-11-methoxy-$O^6,O^7$-bis-ethoxy-carbonyldaunomycinone 5 Grams of 4-demethoxy-4-hydroxy-$O^6,O^7$-bis-ethoxy-carbonyldaunomycinone were dissolved in 100 ml. of dichloromethane and treated with 1.5 ml. of methyl iodide and 1.5 g. of silver oxide. After refluxing for 2 hours, the reaction mixture was filtered and evaporated to a residue. The residue was chromatographed (silica gel; dichloromethane) to afford pure 4-demethoxy-4-hydroxy-11-deoxy-11-methoxy-$O^6,O^7$-bis-ethoxycarbonyldaunomycinone.

PMR (CDCl$_3$): 1.33 and 1.46δ(two t, CH$_3$-C(H$_2$)), 2.36δ(s, CH$_3$CO), 3.83δ(s, CH$_3$O), 4.23 and 4.36δ(two q, CH$_2$-C(H$_3$)), 6.13δ(broad s, C-7-H), 7.0-7.8δ(m, 3 aromatic protons), 12. 2δ(s, phenolic hydroxyl).

IR (KBr): 1765, 1740, 1715, 1675, 1635, 1580 cm$^{-1}$.

EXAMPLE 2

4-Demethoxy-4-hydroxy-7,11-bis-deoxy-7,11-bis-methoxydaunomycinone

A solution of 1.5 g of 4-demethoxy-4-hydroxy-11-deoxy-11-methoxy-$O^6,O^7$-bis-ethoxycarbonyl-daunomycinone in a 1:1 mixture of dichloromethane-methanol was treated with an excess of AG1-X2 resin which had been previously activated with aqueous sodium hydroxide and washed with methanol. The reaction mixture was stirred until the starting material had completely disappeared, and then was filtered and evaporated to a residue which was chromatographed (silica gel; chloroform:acetone 95:5, v/v) to give 4-demethoxy-4-hydroxy-7,11-bis-deoxy-7,11-bis-methoxydaunomycinone.

PMR (CDCl$_3$): 2.40δ(s, CH$_3$CO), 3.56 and 3.80δ(two s, two CH$_3$O), 4.85δ(broad s, C-7-H), 6.9–8.3δ(m, 3 aromatic protons), 11.7 and 12.9δ(two s, phenolic hydroxyls).

IR (KBr): 1716, 1670, 1622, 1598 and 1585 cm$^{-1}$.

EXAMPLE 3

4-Demethoxy-4-hydroxy-11-deoxy-11-methoxydaunomycinone and its 7-epimer 1.2 Grams of 4-demethoxy-4hydroxy-7,11-bis-deoxy-7,11-dimethoxydaunomycinone were dissolved in 40 ml. of trifluoroacetic acid containing 2% of water, and the resulting solution was left to stand overnight at room temperature. After removal of the solvet in vacuo, the residue was dissolved in acetone and hydrolyzed with concentrated aqueous ammonia. The reaction mixture was diluted with chloroform, washed with water and evaporated to a residue which was chromatographed to afford two products: 4-demethoxy-4-hydroxy-11-deoxy-11-methoxydaunomycinone (Rf=0.54 on silica gel plate; chloroform:acetone 4:1, v/v) and its 7-epimer (Rf=0.3). If desired, the 7-empimer can be converted to the natural configuration by treatment with dilute trifluoroacetic acid. PMR and IR of 4-demethoxy-4-hydroxy-11-deoxy-11methoxydaunomycinone:

PMR (CDCl$_3$): 2.45δ(s, CH$_3$CO), 3.96δ(s, CH$_3$O), 5.27δ(broad s, c-7-H), 7.0-7.9δ(m, 3 aromatic protons), 11.7 and 13.0δ(two s, phenolic hydroxyls).

IR (KBr): 1715, 1670, 1625, 1600 and 1580 cm$^{-1}$.

EXAMPLE 4

4-Demethoxy-4-hydroxy-11-methoxydaunomycinone and its 7-epimer

The two compounds named above were obtained directly by treatment of 4-demethoxy-4-hydroxy-11-deoxy-11-methoxy-$O^6$, $O^7$-bis -ethoxycarbonyl-daunomycinone with AG1-X2 resin as described in Example 3, but carrying out the reaction in aqueous dichloromethane instead of methanolic dichloromethane and using wet resin.

EXAMPLE 5

4-Demethoxy-4-hydroxy-11-deoxy-11-methoxy-N-trifluoroacetyldaunomycin

To a solution of 1.5 g. of 4-demethoxy-4-hydroxy-11-deoxy-11-methoxydaunomycinone and 1.25 g. of 2,3,6-trideoxy-3-trifluoroacetamido-4-O-trifluoraecetyl-α-L-lyxopyranosyl chloride (1-chloro-N,O-bis-trifluoroacetyldaunosamine) in 100 ml. of anhydrous dichloromethane, a solution of 0.95 g. of silver trifluoromethanesulphonate in anhydrous diethyl ether was added dropwise at room temperature under stirring. After 1 hour the reaction mixture was washed with aqueous NaHCO$_3$ and evaporated to a residue which was dissolved in methanol containing a catalytic amount of triethylamine and left to stand at room temperature for two hours. The solvent was removed in vacauo and the residue chromatographed (silica gel chloroform-acetone 95:5, v/v) to give 4-demethoxy-4-hydroxy-11-deoxy-11-methoxy-N-trifluoroacetyl-daunomycin.

PMR (CDCl$_3$): 1.29δ(d, CH$_3$-C(H), 2.40δ(1, CH$_3$CO), 3.83δ(s, CH$_3$O), 5.15δ(s, C-7-H), 5.39δ(s,C-1'-

H), 7.0–8.0δ(m, NH and aromatic H), 11.76 e 13.04δ(2s, phenolic H).

EXAMPLE 6

4-Demethoxy-4-hydroxy-11-deoxy-11-methoxydaunomycin hydrochloride 0.9 Gram of 4-demethoxy-4hydroxy-11-deoxy-11-methoxy-N-trifluoroacetyldaunomycin was dissolved in 40 ml. of aqueous 0.15 N NaOH and left to stand 1 hour at room temperature. After acidification with oxalic acid and rapid neutralization with aqueous NaHCO$_3$, the product was extracted with chloroform and the organic solution was evaporated to a residue which was dissolved in dichlororomethane and treated with 1 equivalent of HCl in methanol. By addition of diethyl ether, 4-demethoxy-4-hydroxy-11-deoxy-11-methoxydaunomycin hydrochloride was precipitated and collected by filtration.

Rf=0.38 (CHCl$_3$-CH$_3$OH-H$_2$O=13:6:1 v/v)

M.P.: 174°–176° C. dec.;λmax=446 nm.

BIOLOGICAL ACTIVITY

The compound: 4-demethoxy-4hydroxy-11-deoxy-11-methoxy-daunomycin was tested under the auspices of N.C.I., National Institute of Health, Bethesda, Maryland, U.S.A., against Lymphocitic Leukemia P$_{388}$ according to the procedure described in Cancer Chemotherapy Reports, Part 3, Vol. 3, page 9 (1972). The following table illustrates the antitumor activity thereof.

The above compound was compared to daunomycin in a test consisting of mice infected with tumor cells: the injections were made on days 5, 9 and 13 with a 4 day interval between each single injection starting from the fifth day from the tumor transplantation in mice.

TABLE

| Compound | Schedule of Treatment in days (i.p.) | Dose mg./kg. | T/C % |
|---|---|---|---|
| Daunomycin . HCl | 5,9,13 | 32.00 | |
| | | 16.00 | 86 |
| | | 8.00 | 108 |
| | | 4.00 | 134 |
| | | 2.00 | 131 |
| 4-Demethoxy-4-hydroxy-11-deoxy-11-methoxy-daunomycin . HCl | 5,9,13 | 50.00 | 125 |
| | | 25.00 | 122 |
| | | 12.50 | 119 |
| | | 6.25 | 119 |
| | | 3.13 | 118 |

Variations and modifications can, of course, be made without departing from the spirit and scope of the invention.

Having thus described our invention, what we desire to secure by Letters Patent and hereby claim is:

1. A compound of the formula II:

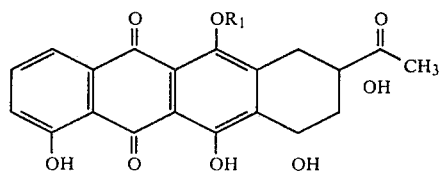

wherein R$_1$ is a lower alkyl having from 1 to 4 carbon atoms.

2. A process for preparing a daunomycinone derivative of the formula:

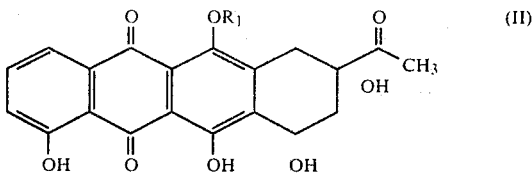

wherein R$_1$ is a lower alkyl group having 1 to 4 carbon atoms, by (a) reacting a compound of formula:

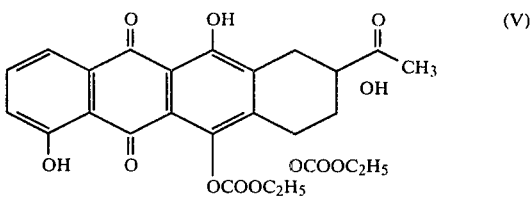

with a halide of the general formula R$_1$-Y wherein R$_1$ is a lower alkyl group having 1 to 4 carbon atoms and Y is Cl, Br or I in the presence of a solvent selected from the group consisting of dichloromethane and chloroform, and in the presence of about one equivalent of a base to yield the monoether derivative of the formula:

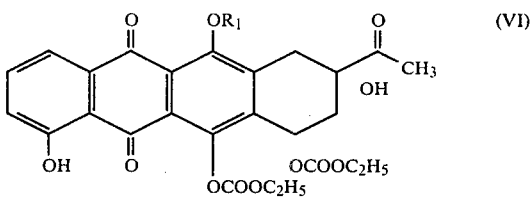

(b) reacting the compound of Formula VI in the presence of a solvent selected from the group consisting of aqueous solvents and alcohols with a base selected from the group consisting of a dilute alkaline hydroxide and an activated basic resin to yield in case of an aqueous medium the compound of the formula:

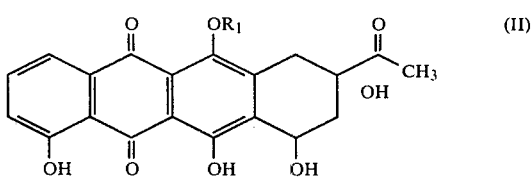

wherein R$_1$ is as defined above; and in case of an alcoholic medium to yield a bis-phenol derivative of the formula:

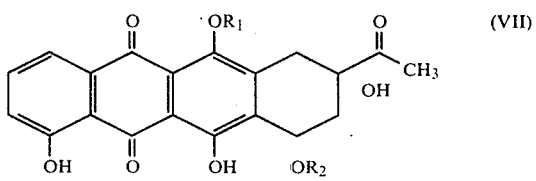

wherein $R_2$ is as defined above and $R_2$ is an alkyl group;

(c) hydrolyzing the compound of Formula VII, formed when the solvent is an alcohol, in aqueous trifluoroacetic acid to yield the compound of Formula II.

3. A process according to claim 1, wherein the base in step (a) is silver oxide and the aqueous medium in step (b) is aqueous dichloromethane.

4. A process according to claim 1, wherein the alcoholic medium in step (b) is alcoholic dichloromethane or methanol.

* * * * *

UNITED STATES PATENT AND TRADEMARK OFFICE
CERTIFICATE OF CORRECTION

PATENT NO. : 4,267,116          Page 1 of 14
DATED : May 12, 1981
INVENTOR(S) : Paolo Masi et al.

It is certified that error appears in the above—identified patent and that said Letters Patent is hereby corrected as shown below:

Title Page, Abstract:" 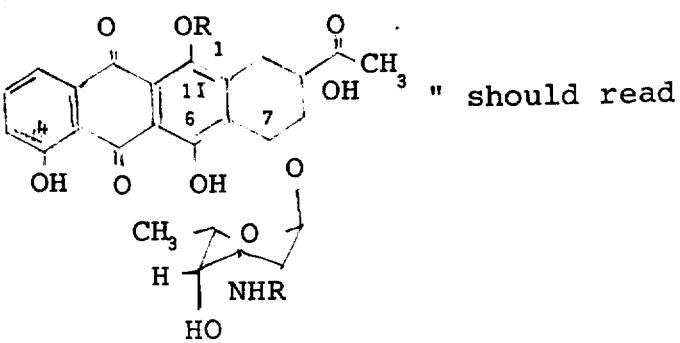 " should read

-- 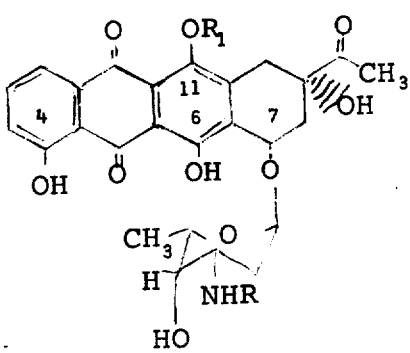 --.

UNITED STATES PATENT AND TRADEMARK OFFICE
CERTIFICATE OF CORRECTION

PATENT NO. : 4,267,116
DATED : May 12, 1981
INVENTOR(S) : Paolo Masi et al.

It is certified that error appears in the above—identified patent and that said Letters Patent is hereby corrected as shown below:

Column 1, line 30: " 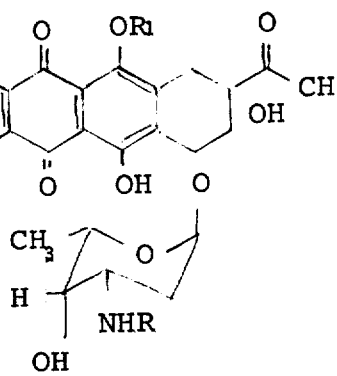 " should read

-- 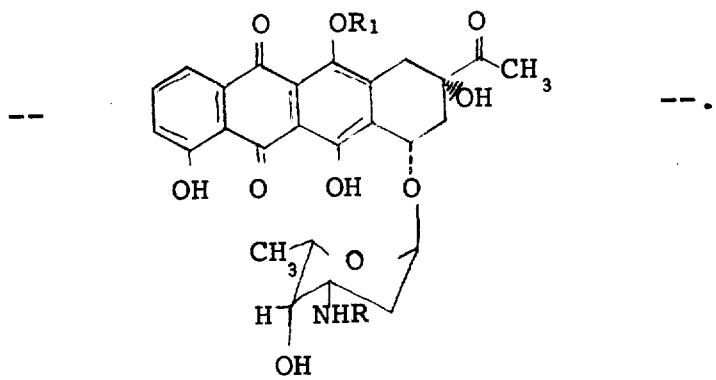 --.

UNITED STATES PATENT AND TRADEMARK OFFICE
CERTIFICATE OF CORRECTION

PATENT NO. : 4,267,116

DATED : May 12, 1981

INVENTOR(S) : Paolo Masi et al.

It is certified that error appears in the above—identified patent and that said Letters Patent is hereby corrected as shown below:

Column 1, line 50: " 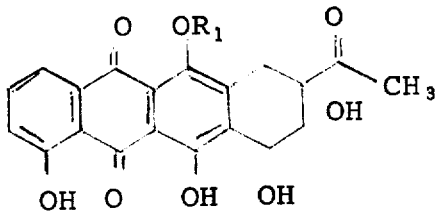 " should read

-- 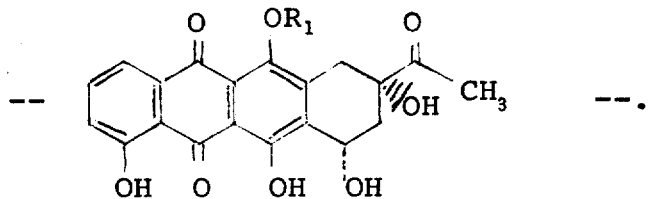 --.

Column 1, line 61: "Ii" should read -- II --.

Column 1, line 67: "4,191,756" should read -- 4,191,755 --.

UNITED STATES PATENT AND TRADEMARK OFFICE
CERTIFICATE OF CORRECTION

PATENT NO. : 4,267,116

Page 4 of 14

DATED : May 12, 1981

INVENTOR(S) : Paolo Masi et al.

It is certified that error appears in the above—identified patent and that said Letters Patent is hereby corrected as shown below:

Column 2, line 5: " 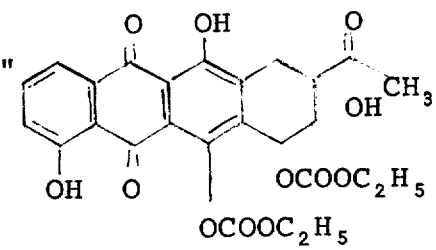 " should read

-- 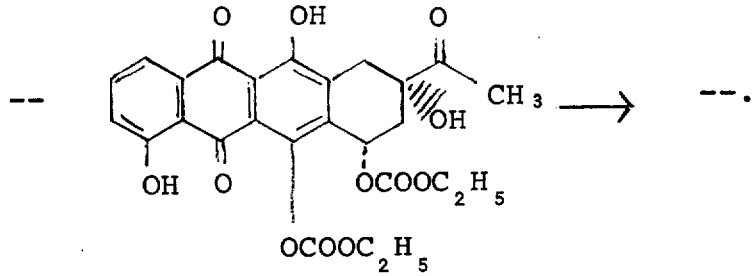 --.

UNITED STATES PATENT AND TRADEMARK OFFICE
CERTIFICATE OF CORRECTION

PATENT NO. : 4,267,116

DATED : May 12, 1981

INVENTOR(S) : Paolo Masi et al.

It is certified that error appears in the above—identified patent and that said Letters Patent is hereby corrected as shown below:

Column 2, line 10: " 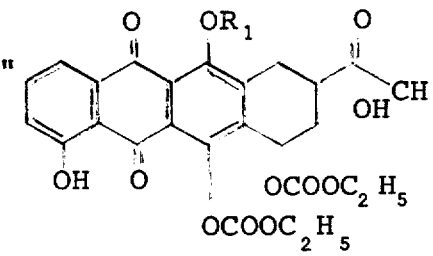 " should read

-- 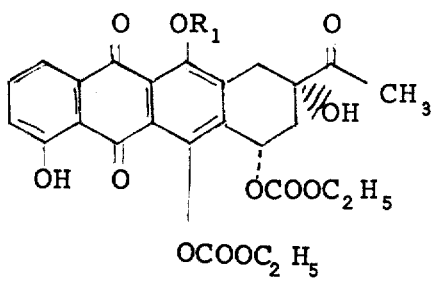 --.

UNITED STATES PATENT AND TRADEMARK OFFICE
CERTIFICATE OF CORRECTION

PATENT NO. : 4,267,116      Page 6 of 14
DATED : May 12, 1981
INVENTOR(S) : Paolo Masi et al.

It is certified that error appears in the above—identified patent and that said Letters Patent is hereby corrected as shown below:

Column 2, line 20:     " 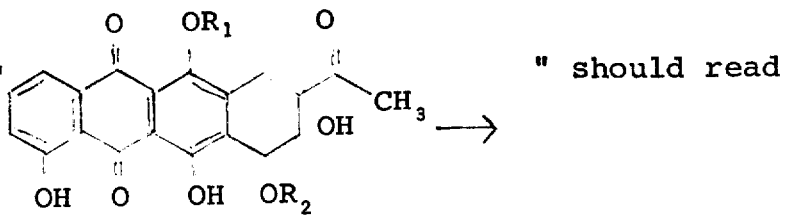     " should read

-- 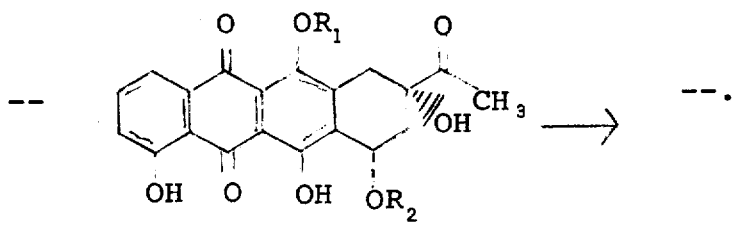 --.

UNITED STATES PATENT AND TRADEMARK OFFICE
CERTIFICATE OF CORRECTION

PATENT NO. : 4,267,116
DATED : May 12, 1981
INVENTOR(S) : Paolo Masi et al.

It is certified that error appears in the above—identified patent and that said Letters Patent is hereby corrected as shown below:

Column 2, line 30:" 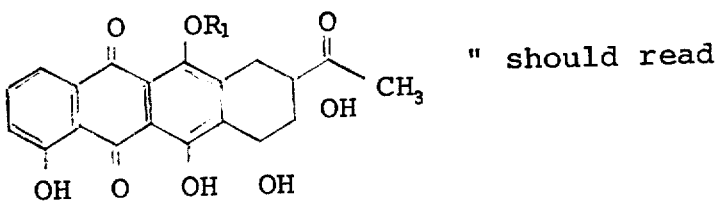 " should read

-- 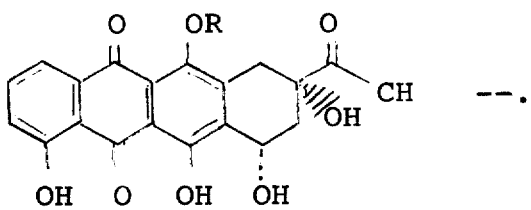 --.

Column 2, line 58: "Ii" should read -- II --.

UNITED STATES PATENT AND TRADEMARK OFFICE
CERTIFICATE OF CORRECTION

PATENT NO. : 4,267,116
DATED : May 12, 1981
INVENTOR(S) : Paolo Masi et al.

It is certified that error appears in the above—identified patent and that said Letters Patent is hereby corrected as shown below:

Column 3, line 5: " 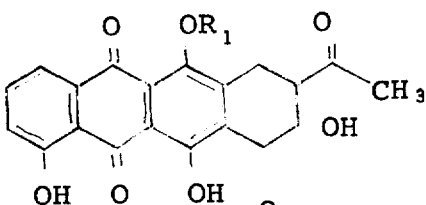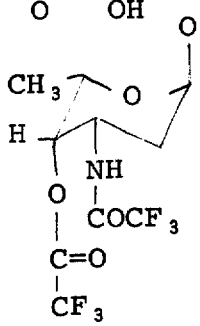 " should read

-- 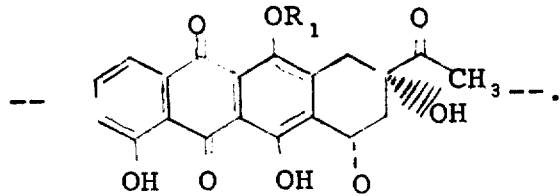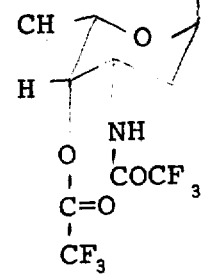 --.

UNITED STATES PATENT AND TRADEMARK OFFICE
CERTIFICATE OF CORRECTION

PATENT NO. : 4,267,116
DATED : May 12, 1981
INVENTOR(S) : Paolo Masi et al.

It is certified that error appears in the above—identified patent and that said Letters Patent is hereby corrected as shown below:

Column 4, line 26: "empimer" should read -- epimer --.

Column 4, line 36: "4 hydroxy-11-methoxydaunomycinone" should read -- 4 hydroxy-11-deoxy-11-methoxydaunomycinone"--.

Column 4, line 63: "vacauo" should read -- vacuo --.

Column 5, line 60: " 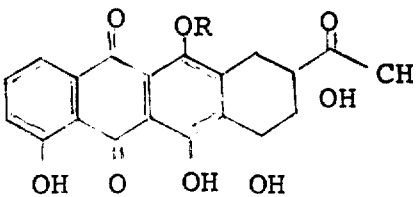 " should read

-- 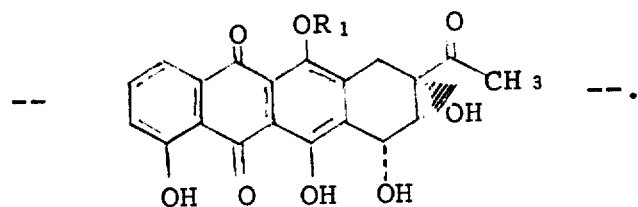 --.

UNITED STATES PATENT AND TRADEMARK OFFICE
CERTIFICATE OF CORRECTION

PATENT NO. : 4,267,116

Page 10 of 14

DATED : May 12, 1981

INVENTOR(S) : Paolo Masi et al.

It is certified that error appears in the above—identified patent and that said Letters Patent is hereby corrected as shown below:

Column 6, line 5: " 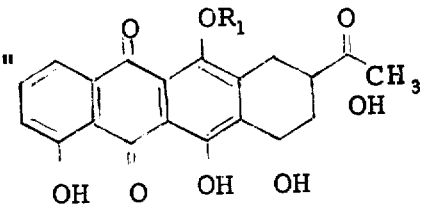 " should read

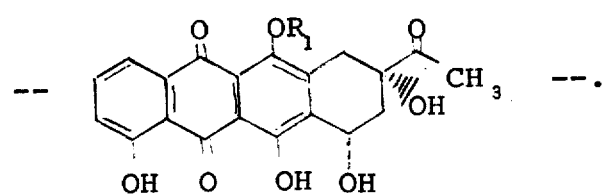 --.

UNITED STATES PATENT AND TRADEMARK OFFICE
CERTIFICATE OF CORRECTION

PATENT NO. : 4,267,116

DATED : May 12, 1981

INVENTOR(S) : Paolo Masi et al.

It is certified that error appears in the above—identified patent and that said Letters Patent is hereby corrected as shown below:

Column 6, line 20: " 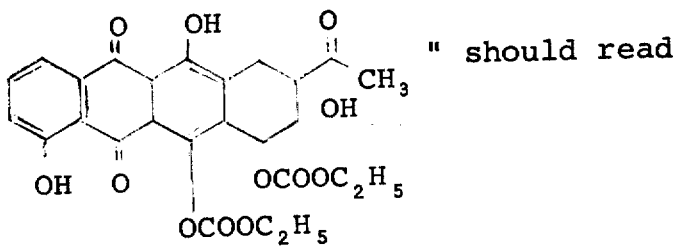 " should read

-- 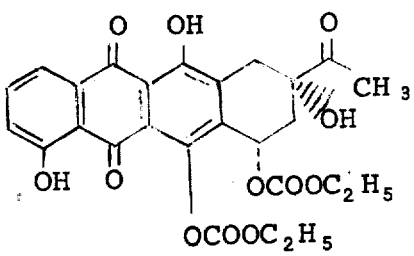 --.

UNITED STATES PATENT AND TRADEMARK OFFICE
CERTIFICATE OF CORRECTION

PATENT NO. : 4,267,116
DATED : May 12, 1981
INVENTOR(S) : Paolo Masi et al.

It is certified that error appears in the above—identified patent and that said Letters Patent is hereby corrected as shown below:

Column 6, line 35: " 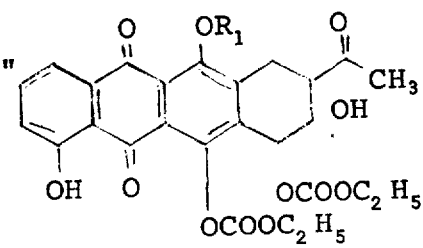 " should read

-- 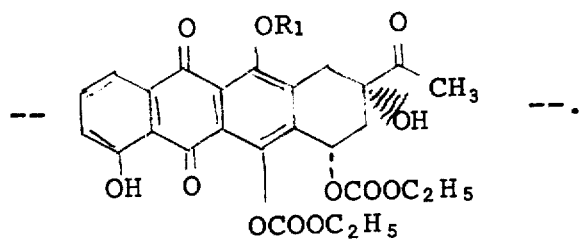 --.

UNITED STATES PATENT AND TRADEMARK OFFICE
CERTIFICATE OF CORRECTION

PATENT NO. : 4,267,116

DATED : May 12, 1981

INVENTOR(S) : Paolo Masi et al.

It is certified that error appears in the above—identified patent and that said Letters Patent is hereby corrected as shown below:

Column 6, line 50: " 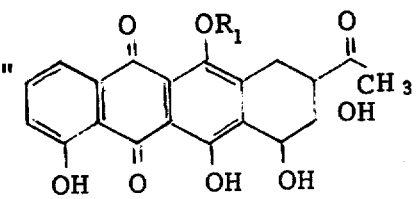 " should read

-- 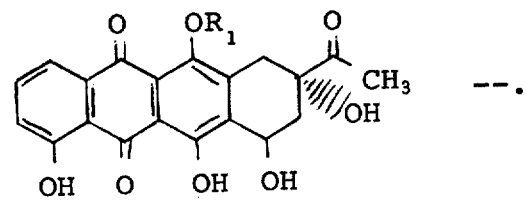 --.

UNITED STATES PATENT AND TRADEMARK OFFICE
CERTIFICATE OF CORRECTION

PATENT NO. : 4,267,116

DATED : May 12, 1981

INVENTOR(S) : Paolo Masi et al.

It is certified that error appears in the above—identified patent and that said Letters Patent is hereby corrected as shown below:

Column 6, line 65: " 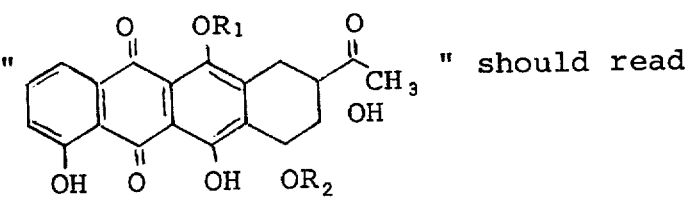 " should read

-- 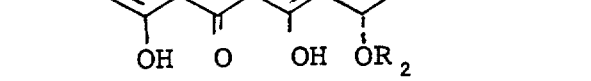 --.

Signed and Sealed this

Tenth Day of November 1981

[SEAL]

Attest:

GERALD J. MOSSINGHOFF

Attesting Officer

Commissioner of Patents and Trademarks